(12) United States Patent
Voic

(10) Patent No.: US 10,117,666 B2
(45) Date of Patent: Nov. 6, 2018

(54) ULTRASONIC INSTRUMENT AND METHOD USING SAME

(71) Applicant: MISONIX INCORPORATED, Farmingdale, NY (US)

(72) Inventor: Dan Voic, Cedar Grove, NJ (US)

(73) Assignee: MISONIX INC., Farmingdale, NY (US)

( * ) Notice: Subject to any disclaimer, the term of this patent is extended or adjusted under 35 U.S.C. 154(b) by 1038 days.

(21) Appl. No.: 14/038,463

(22) Filed: Sep. 26, 2013

(65) Prior Publication Data

US 2015/0088179 A1 Mar. 26, 2015

(51) Int. Cl.
*A61B 17/32* (2006.01)
*A61B 90/00* (2016.01)

(52) U.S. Cl.
CPC ........ *A61B 17/320068* (2013.01); *A61B 2090/0803* (2016.02); *A61B 2090/0807* (2016.02)

(58) Field of Classification Search
CPC ........... A61B 19/00; A61B 17/320068; A61B 2019/486; A61B 2018/00988
USPC ........................................ 600/407; 606/169
See application file for complete search history.

(56) References Cited

U.S. PATENT DOCUMENTS

| | | | |
|---|---|---|---|
| 3,542,519 A * | 11/1970 | Kedzie | A46B 15/0002 116/200 |
| 3,990,452 A | 11/1976 | Murry et al. | |
| 4,886,009 A * | 12/1989 | Gondar | B23D 51/025 116/208 |
| 5,318,520 A | 6/1994 | Nakao | |
| 5,546,624 A * | 8/1996 | Bock | A46B 7/04 15/167.1 |
| 5,906,834 A * | 5/1999 | Tseng | A46B 11/00 15/104.93 |
| 6,167,833 B1 * | 1/2001 | Caraway | E21B 12/02 116/208 |
| 6,314,907 B1 * | 11/2001 | Harris | A46B 15/0002 116/200 |
| 6,957,622 B2 | 10/2005 | Boettcher et al. | |
| 7,976,569 B2 | 7/2011 | Justis | |
| 8,025,672 B2 * | 9/2011 | Novak et al. | 606/169 |
| 2005/0081971 A1 * | 4/2005 | Heinen | B60C 11/032 152/209.1 |
| 2005/0273126 A1 * | 12/2005 | Beaupre | A61B 17/320068 606/169 |
| 2006/0187003 A1 * | 8/2006 | Terenna | G04F 1/005 340/309.16 |

(Continued)

*Primary Examiner* — David C Eastwood
(74) *Attorney, Agent, or Firm* — R. Neil Sudol; Henry D. Coleman

(57) ABSTRACT

An ultrasonic medical instrument includes a probe shaft having a threaded coupling at a proximal end and an end effector or head at a distal end. The coupling is configured for operative attachment to a source of ultrasonic mechanical vibratory energy, while the head has an operative surface configured for engagement with organic tissues of a patient. The probe shaft, the coupling, and the head are made of a metal or metal alloy. At least one end-of-life indicator element is affixed to the probe shaft or head, the indicator element being made of a material that gradually disintegrates or degrades with use of the instrument so as to provide a visible indicator of degree of use and remaining useful life of the instrument.

16 Claims, 1 Drawing Sheet

(56) References Cited

U.S. PATENT DOCUMENTS

2006/0269901 A1* 11/2006 Rosenblood ............. A61C 1/07
433/166
2007/0011836 A1* 1/2007 Brewer .............. A46B 15/0002
15/220.1

* cited by examiner

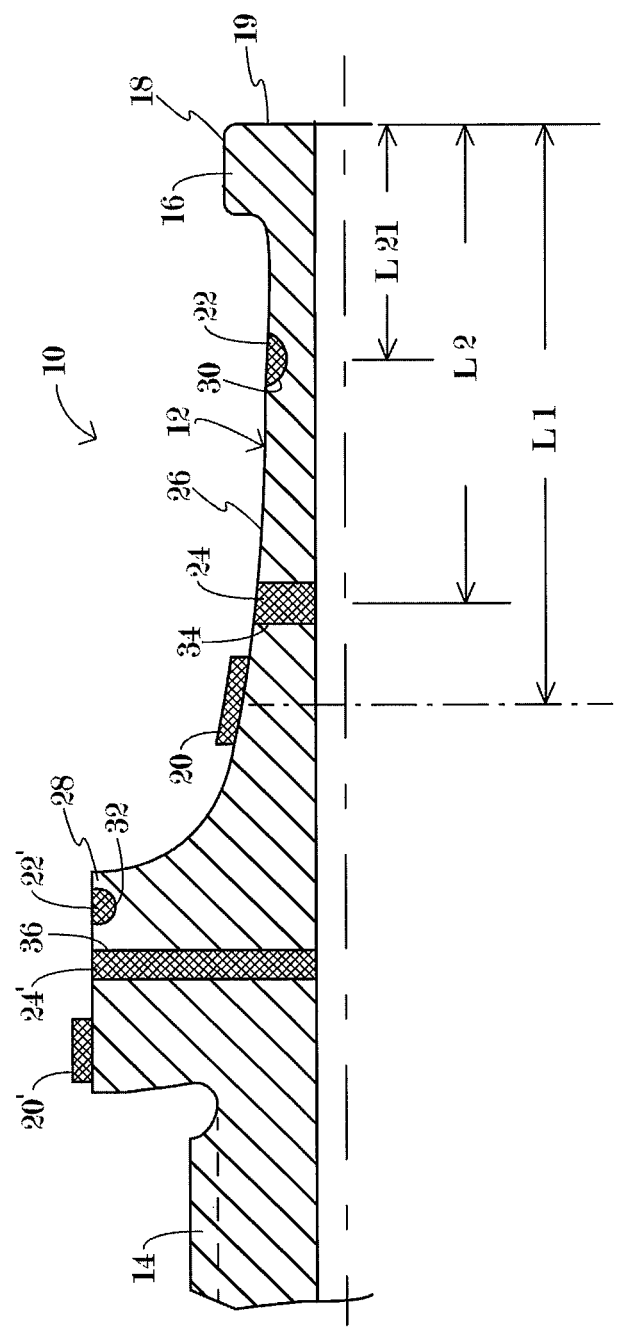

ULTRASONIC INSTRUMENT AND METHOD USING SAME

BACKGROUND OF THE INVENTION

This invention relates to an ultrasonic tool or instrument particularly, but not exclusively, for use in medical surgical procedures. This invention also relates to an associated process using the ultrasonic instrument or tool Ultrasonic tools have become increasingly used in surgical procedures. Ultrasonic ablation tools are recognized for their accuracy, reliability and ease of use. Ultrasonic bone cutting blades may be designed to facilitate the cutting of bone without damage to adjacent soft tissues. See U.S. Pat. No. 8,343,178. Ultrasonic debriders remove necrotic or otherwise damaged tissue without harming underlying healthy tissue. Ultrasonic instruments such as debriders can have integrated tissue treatment modalities such as high-energy electrical current transmission for cauterization (See U.S. Pat. No. 6,648,839) and low-energy electrical energy transmission for pain suppression (U.S. Patent Application Publication No. 2008/0146921) or stimulating tissue repair (U.S. Pat. No. 8,025,672).

In the field of orthopedics, the cutting of living bone is a prerequisite for many procedures. Such procedures include the reconstruction of damaged tissue structures due to accidents, the grafting of healthy bone into areas damaged by disease, or the correction of congenital facial abnormalities like a receding chin line.

Ultrasonic tools like all other tools are subject to fatigue stressing and wear. An ultrasonic medical instrument may be in use so long as to degrade or exhibit irregularities in a cutting edge. Fatigue stress may make the instrument prone to failure at an inopportune moment. An uneven cutting edge may result in undesirable damage to target tissues.

OBJECTS OF THE INVENTION

It is an object of the present invention to provide an ultrasonic instrument with means for preventing or reducing the chances of sudden failure.

A related object of the present invention is to provide an ultrasonic medical instrument with means for preventing or reducing damage to organic tissues arising from instrument wear or fatigue.

A more particular object of the present invention is to provide an ultrasonic medical instrument with such means that are easy to monitor by medical personnel.

A further object of the present invention is to provide an associated method for instrument use wherein potential damage to organic tissues of a patient is obviated or avoided.

These and other objects of the present invention will be apparent from the descriptions and drawings herein. Although every object of the invention is attainable by at least one embodiment of the invention, there is not necessarily any single embodiment that achieves all of the objects of the invention.

SUMMARY OF THE INVENTION

An ultrasonic medical instrument in accordance with the present invention comprises a probe shaft having a connector at a proximal end and a head at a distal end. The connector (generally a threaded coupling) is configured for operative attachment to a source of ultrasonic mechanical vibratory energy, while the head has an operative surface configured for engagement with organic tissues of a patient. The probe shaft, the connector, and the head are made of a rigid first material, typically a metal or metal alloy but possibly a ceramic. At least one end-of-life indicator element is affixed to the probe shaft or possibly the head, the indicator element being made of a second material that gradually disintegrates or degrades with use of the instrument so as to provide a visible indicator of degree of use and remaining useful life of the instrument.

The indicator element material may be a ceramic or a polymeric material. The indicator element material is biocompatible and preferably biodegradable. Accordingly, where material is shed from the indicator element during use thereof in contact with organic tissues of a patient, the shed material is accommodated by the body.

The end-of-life indicator element may be fastened (e.g., adhesively) to an exterior surface of the one of the probe shaft and the head. Alternatively, the end-of-life indicator element may be inserted or disposed in a recess formed in an exterior surface of the one of the probe shaft and the head.

The end-of-life indicator element may be a primary indicator element, with a secondary or auxiliary indicator being provided that is initially hidden by the primary end-of-life indicator element and that becomes visible once the primary indicator element degrades or disintegrates sufficiently to reveal the auxiliary indicator.

The ultrasonic medical instrument may take any form, including, but not limited to, bone cutting blades, wound debriders, liposuction probes, etc.

The end-of-life indicator element and the location thereof on the ultrasonic instrument may be coordinated so that a visible disintegration or degradation of the indicator element effectively marks (coincides with) the end of the useful life of the ultrasonic instrument. In addition, the size of the indicator element may be varied within limits to adjust the rate of disintegration or degradation of the indicator element. Typically, the end-of-life indicator element is affixed to the one of the probe shaft and the head at a preselected location within one-half an operating wavelength of a distal end of the instrument.

A medical method in accordance with the present invention utilizes an ultrasonic medical instrument having an end-of-life indicator element affixed to one of the probe shaft and the head, the indicator element being made of a material that gradually disintegrates with use of the instrument. The method comprises applying an active or operative surface of the instrument to organic tissues of different patients (in successive surgical operations), activating the instrument with ultrasonic mechanical vibratory energy during the applying of the active or operative surface to the respective organic tissues, periodically monitoring the end-of-life indicator element over multiple uses of the instrument, each use on organic tissues of a respective one of the patients, and retiring the instrument from medical use upon detecting a predetermined amount of disintegration of the end-of-life indicator element.

Where the end-of-life indicator element is made of a biocompatible and biodegradable material, the disintegration of the end-of-life indicator element includes dissolving material of the end-of-life indicator element into patients' organic tissues.

BRIEF DESCRIPTION OF THE DRAWING

The sole FIGURE of the drawing is a schematic longitudinal quarter cross-sectional view of an ultrasonic instrument in accordance with the present invention, showing a plurality of end-of-life elements.

DETAILED DESCRIPTION

As illustrated in the drawing, an ultrasonic medical instrument 10 comprises a probe shaft 12 having a connector 14 at a proximal end and a head 16 at a distal end. Connector 14 takes the form of an externally threaded coupling configured for operative attachment to a source of ultrasonic mechanical vibratory energy. Typically, the vibration source is an electromechanical transducer device including a stack of piezoelectric crystal wafers. Head 16 has an operative surface 18 and/or 19 configured for engagement with organic tissues of a patient. Probe shaft 12, connector 14, and head 16 are made of a rigid material, typically a metal or metal alloy but possibly a ceramic. Instrument 10 is provided with one or more end-of-life indicator elements 20, 20', 22, 22', 24, 24' affixed to probe shaft 12 or possibly head 16. Indicator elements 20, 20', 22, 22', 24, 24' are each made of a material that gradually disintegrates or degrades with use of instrument 10—at a rate faster than a rate of disintegration of the material of probe shaft 12)—so as to provide a visible indicator of degree of use and remaining useful life of the instrument.

Indicator elements 20 and 20' are fastened (e.g., adhesively) to an exterior surface 26 or 28 of probe shaft 12. Indicator elements 22 and 22' are disposed in respective shallow recesses 30 and 32 formed in exterior surfaces 26 and 28 probe shaft 12. Indicator elements 24 and 24' are disposed in respective deep recesses or bores 34 and 36 formed in exterior surfaces 26 and 28 probe shaft 12.

Any particular ultrasonic instrument 10 typically includes only one or two of the end-of-life indicator elements 20, 20', 22, 22', 24, 24'. Multiple indicator elements 20, 20', 22, 22', 24, 24' ensure that users detect the erosion of at least one indicator element. Multiple end-of-life indicator elements 20, 20', 22, 22', 24, 24' may be used that are designed to provide visual indicators after different degrees of accumulated use. Thus, a first indicator element may signal that the expected life of the instrument 10 is 75% used, while another indicates that 90% of the expected life has been used.

End-of-life indicator elements 20, 20', 22, 22', 24, 24' may be made of a ceramic or a polymeric material. In any case, indicator elements 20, 20', 22, 22', 24, 24' are biocompatible and preferably biodegradable. Accordingly, where material is shed from indicator elements 20, 20', 22, 22', 24, 24' during use thereof in contact with organic tissues of a patient, the shed material is absorbed and metabolized by the body.

End-of-life indicator elements 20, 20', 22, 22', 24, 24' may each be a primary indicator element, with a secondary or auxiliary indicator being provided underneath, on probe shaft surface 26 or 28, that is initially hidden by the primary end-of-life indicator element and that becomes visible once the primary indicator element degrades or disintegrates sufficiently to reveal the auxiliary indicator. Examples of auxiliary indicators are symbols such as a stop sign or a do-not-enter sign, a word such as "recycle" or "discard," a graphic such as a skull and bones representation, and a color tab, such as a red dot, stripe or circle (e.g., when inside a cylindrical recess).

Instrument 10 exemplarily takes the form of a bone cutting blade, a wound debrider, a liposuction probe, etc.

End-of-life indicator elements 20, 20', 22, 22', 24, 24' and the locations thereof on instrument 10 may be coordinated so that a visible disintegration or degradation of the indicator element effectively coincides with the end of the useful life of the ultrasonic instrument. For instance, where an end-of-life indicator element 20, 20', 22, 22', 24, 24' is made of a material that erodes or disintegrates slowly, the indicator is preferably positioned at or near a vibration node as determined by the instrument geometry and the characteristic operating frequency. Alternatively, where the end-of-life indicator is made of a material that erodes or disintegrates relatively quickly, the indicator is preferably positioned at or near a vibration anti-node as determined by the instrument geometry and the characteristic operating frequency. In addition, the size of the indicator element may be varied within limits to adjust the rate of disintegration or degradation of the indicator element. Typically, an end-of-life indicator element 20, 22, 24 is affixed to probe shaft 12 at a preselected location within one-half an operating wavelength of a distal end of the instrument. The drawing FIGURE shows indicator element 22 disposed at a distance $L_{21}$ less than a one-quarter wavelength from the distal tip (surface 19) of instrument 10, indicator element 24 disposed at a distance $L_2$ less than a one-half wavelength from the distal tip (19), and indicator element 20 disposed at a distance $L_1$ about one-half wavelength from the distal tip (19).

A method of use of instrument 10 comprises applying an active or operative surface 18 or 19 of the instrument to organic tissues of different patients in successive surgical operations over an extended period of time, and activating the instrument with ultrasonic mechanical vibratory energy or a pre-established ultrasonic frequency during contact of the active or operative surface 18, 19 with the respective organic tissues. One periodically monitors the end-of-life indicator element 20, 20', 22, 22', 24, and/or 24' over multiple uses of the instrument, each use on organic tissues of a respective one of the patients. The instrument is retired from medical use upon one's detecting a predetermined amount of disintegration of one or more of the end-of-life indicator elements 20, 20', 22, 22', 24, and 24'.

Where the end-of-life indicator element is made of a biocompatible and biodegradable material, the disintegration of the end-of-life indicator element includes dissolving material of the end-of-life indicator element into patients' organic tissues.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An ultrasonic medical instrument comprising:
    a probe shaft having a connector at a proximal end and a head at a distal end, the connector being configured for operative attachment to a source of ultrasonic mechanical vibratory energy, the head having an operative surface configured for engagement with organic tissues of a patient, said probe shaft, said connector, and said head being made of a rigid first material; and
    at least one end-of-life indicator element affixed to one of said probe shaft and said head, said indicator element including a layer of a second material that disintegrates or degrades with repeated use of the instrument, said indicator element further including an alphanumeric or graphic symbol hidden by said layer and revealed upon a disintegration or degrading of said layer upon repeated use of the instrument.

2. The ultrasonic medical instrument defined in claim 1 wherein said second material is a biocompatible material.

3. The ultrasonic medical instrument defined in claim 2 wherein said second material is a biodegradable material.

4. The ultrasonic medical instrument defined in claim 1 wherein said first material is taken from the group consisting of metal and alloy, said second material being taken from the group consisting of polymeric and ceramic material.

5. The ultrasonic medical instrument defined in claim 1 wherein said end-of-life indicator element is fastened to an exterior surface of said one of said probe shaft and said head.

6. The ultrasonic medical instrument defined in claim 1 wherein said end-of-life indicator element is disposed in a recess formed in an exterior surface of said one of said probe shaft and said head.

7. The ultrasonic medical instrument defined in claim 1 wherein said end-of-life indicator element is affixed to said one of said probe shaft and said head at a preselected location within one-half an operating wavelength of a distal end of said instrument.

8. The ultrasonic medical instrument defined in claim 1 wherein said symbol has a meaning directing a user to cease or terminate further use of the instrument.

9. The ultrasonic medical instrument defined in claim 8 wherein said symbol is taken from the group consisting of a stop sign, a do-not-enter sign, the word "recycle", the word "discard," and a skull and bones representation.

10. The ultrasonic medical instrument defined in claim 1 wherein said end-of-life indicator element is affixed to said one of said probe shaft and said head at a preselected location within one-half an operating wavelength of a distal end of said instrument.

11. An ultrasonic medical instrument comprising:
a probe shaft having a connector at a proximal end and a head at a distal end, the connector being configured for operative attachment to a source of ultrasonic mechanical vibratory energy, the head having an operative surface configured for engagement with organic tissues of a patient, said probe shaft, said connector, and said head being made of a rigid first material; and
a plurality of separate end-of-life indicator elements affixed to one of said probe shaft and said head, said indicator elements each including a layer of a second material that disintegrates or degrades with repeated use of the instrument, said indicator elements configured to provide visual indicators after different degrees of accumulated use.

12. The ultrasonic medical instrument defined in claim 11 wherein a first of said plurality of indicator elements signals that the expected life of the instrument has been reduced by a first percentage, and wherein a second of said plurality of indicator elements signals that the expected life of the instrument has been reduced by a second percentage greater than said first percentage.

13. The ultrasonic medical instrument defined in claim 11 wherein said second material is a biocompatible material.

14. The ultrasonic medical instrument defined in claim 13 wherein said second material is a biodegradable material.

15. The ultrasonic medical instrument defined in claim 11 wherein said first material is taken from the group consisting of metal and alloy, said second material being taken from the group consisting of polymeric and ceramic material.

16. The ultrasonic medical instrument defined in claim 11 wherein each of said plurality of end-of-life indicator elements is fastened to an exterior surface of said one of said probe shaft and said head.

* * * * *